(12) United States Patent
Johansson (10) Patent No.: US 9,125,774 B2
(45) Date of Patent: Sep. 8, 2015

(54) ABSORBENT ARTICLE

(75) Inventor: Charlotte Johansson, Göteborg (SE)

(73) Assignee: SCA HYGIENE PRODUCTS AB, Göteborg (SE)

(*) Notice: Subject to any disclaimer, the term of this patent is extended or adjusted under 35 U.S.C. 154(b) by 0 days.

(21) Appl. No.: 14/113,080

(22) PCT Filed: Dec. 17, 2010

(86) PCT No.: PCT/SE2010/051417
§ 371 (c)(1),
(2), (4) Date: Oct. 21, 2013

(87) PCT Pub. No.: WO2012/082037
PCT Pub. Date: Jun. 21, 2012

(65) Prior Publication Data
US 2014/0066876 A1    Mar. 6, 2014

(51) Int. Cl.
*A61F 13/15*        (2006.01)
*A61F 13/551*       (2006.01)
(Continued)

(52) U.S. Cl.
CPC ........... *A61F 13/5514* (2013.01); *A61F 13/475* (2013.01); *A61F 13/47272* (2013.01); *A61F 13/55135* (2013.01)

(58) Field of Classification Search
CPC ............ A61F 13/551; A61F 13/55105; A61F 13/55115; A61F 13/5513; A61F 13/55135; A61F 13/5514; A61F 13/5515; A61F 13/55155; A61F 13/5516; A61F 13/55165; A61F 13/5519; A61F 13/15747; A61F 13/8402; A61F 13/55195
USPC .................................................... 604/385.02

See application file for complete search history.

(56) References Cited

U.S. PATENT DOCUMENTS 3,973,567 A * 8/1976 Srinivasan et al. ....... 604/385.05
4,433,972 A   2/1984 Malfitano
(Continued)

FOREIGN PATENT DOCUMENTS

CN    1259857 A    7/2000
CN    1302195 A    7/2001
(Continued)

OTHER PUBLICATIONS

Translation of Kinoshita, Oct. 23, 2008, WO 2008/126443.*
(Continued)

*Primary Examiner* — Lynne Anderson
*Assistant Examiner* — Bradley Philips
(74) *Attorney, Agent, or Firm* — Buchanan Ingersoll & Rooney PC (57) ABSTRACT

An absorbent article package (1) including an absorbent article (2) and a wrapper (3). The absorbent article (2) includes a backsheet (4), a liquid permeable first layer (5) and an absorbent body (6) therebetween. The wrapper (3) includes an inner surface (11) facing the absorbent article (2) and an outer surface (12) facing away from the absorbent article (2). The absorbent article (2) includes a first leakage barrier side (13) positioned along at least a part of a first longitudinal side edge (7) and a second leakage barrier side (14) positioned along at least a part of a second longitudinal side edge (8). The wrapper (3) includes a first and a second flap (16, 17) being folded over the liquid permeable first layer (5) and attached to each other securing each of the first and second leakage barrier sides (13, 14) in a folded position over a part of the liquid permeable first layer (5).

13 Claims, 10 Drawing Sheets

(51) Int. Cl.
*A61F 13/472* (2006.01)
*A61F 13/475* (2006.01)

(56) References Cited

U.S. PATENT DOCUMENTS

| | | | | |
|---|---|---|---|---|
| 5,478,336 | A * | 12/1995 | Pigneul | 604/385.04 |
| 5,569,228 | A | 10/1996 | Byrd et al. | |
| 5,613,961 | A | 3/1997 | DiPalma et al. | |
| 6,293,932 | B1 * | 9/2001 | Balzar et al. | 604/385.02 |
| 6,312,417 | B1 * | 11/2001 | Hansson | 604/385.02 |
| 8,317,766 | B2 | 11/2012 | Naoto et al. | |
| 8,540,690 | B2 * | 9/2013 | Nomoto et al. | 604/385.04 |
| 2002/0052592 | A1 | 5/2002 | Mills et al. | |
| 2006/0149201 | A1 * | 7/2006 | Sato et al. | 604/385.02 |

FOREIGN PATENT DOCUMENTS

| | | | |
|---|---|---|---|
| CN | 101686882 A | 3/2010 | |
| EP | 2 161 012 A1 | 3/2010 | |
| JP | H09 266928 A | 10/1997 | |
| JP | 2004-261353 A | 9/2004 | |
| JP | 2006-280522 A | 10/2006 | |
| RU | 2257187 C2 | 7/2005 | |
| WO | WO 91/18574 A1 | 12/1991 | |
| WO | 96/23469 A1 | 8/1996 | |
| WO | 99/60965 A1 | 12/1999 | |
| WO | WO 2008/126443 A1 | 10/2008 | |

OTHER PUBLICATIONS

Translation of Kikuchiate, Oct. 19, 2006, JP-2006280522.*
International Search Report (PCT/ISA/210) mailed on Aug. 31, 2011, by the Swedish Patent Office as the International Searching Authority for International Application No. PCT/SE2010/051417.
Written Opinion (PCT/ISA/237) mailed on Aug. 31, 2011, by the Swedish Patent Office as the International Searching Authority for International Application No. PCT/SE2010/051417.
International Preliminary Report on Patentability issued Jun. 18, 2013 by the WIPO for International Application No. PCT/SE2010/051417.
Chinese Office Action (Notification of the First Office Action) dated Jul. 1, 2014, issued by the State Intellectual Property Office of the People's Republic of China in corresponding Chinese Patent Application No. 201080070683.8, and English language translation of Office Action. (9 pages).
Russian Office Action dated Jun. 27, 2014, issued by the Russian Patent Office in corresponding Russian Patent Application No. 2013132942/12(049271), and English language translation of Office Action. (15 pages).
Extended European Search Report issued in corresponding EP 10860867.0, mailed Oct. 2, 2014 (5 pages).
Office Action (Notification of the Second Office Action) issued on Feb. 6, 2015, by the State Intellectual Property Office (SIPO) of the People's Republic of China in corresponding Chinese Patent Application No. 201080070683.8, and an English translation of the Office Action.

* cited by examiner

ABSORBENT ARTICLE

TECHNICAL FIELD

The invention relates to an absorbent article package comprising an absorbent article and a wrapper. The absorbent article comprises a backsheet, a liquid permeable first layer and an absorbent body therebetween. The absorbent article comprises opposing first and second longitudinal side edges and opposing first and second lateral side edges. The wrapper comprises an inner surface facing the absorbent article and an outer surface facing away from the absorbent article. The absorbent article comprises a first leakage barrier side positioned along at least a part of the first longitudinal side edge and a second leakage barrier side positioned along at least a part of the second longitudinal side edge.

BACKGROUND ART

Absorbent articles for absorbing urine are known in prior art to be packaged in a wrapper. WO 91/18574 teaches a releasable wrapper folded about the longitudinal side margins of a sanitary napkin in a C-fold so that both faces of the sanitary napkin are protected. The releasable wrapper and sanitary napkin may be folded about spaced-apart, laterally oriented fold lines to produce a single use package. One problem with such a package and other packages known in prior art is that the unfolded absorbent article is given a flat shape due to the folding. The compression of the article during packaging and storing hinders the article from retaking a cup-shape which is desirable to obtain maximal functionality and the flat shape increases the risk of side leakage during use.

DISCLOSURE OF INVENTION

There is a need for an improved absorbent article package where the problems with prior art is rectified.

The present invention intends to solve the problem by providing an absorbent article package comprising an absorbent article and a wrapper, the absorbent article comprising a backsheet, a liquid permeable first layer and an absorbent body therebetween, the absorbent article comprising opposing first and second longitudinal side edges and opposing first and second lateral side edges, the wrapper comprising an inner surface facing the absorbent article and an outer surface facing away from the absorbent article, the absorbent article comprising a first leakage barrier side positioned along at least a part of the first longitudinal side edge and a second leakage barrier side positioned along at least a part of the second longitudinal side edge, characterized in that the wrapper comprises a cover portion covering the absorbent article and that the wrapper comprises a first and a second flap being folded over the liquid permeable first layer and attached to each other securing each of the first and second leakage barrier sides in a folded position over a part of the liquid permeable first layer.

An absorbent article package according to the invention comprises an absorbent article and a wrapper. The absorbent article comprises a backsheet, a liquid permeable first layer and an absorbent body therebetween. The absorbent article comprises opposing first and second longitudinal side edges and opposing first and second lateral side edges. The wrapper comprises an inner surface facing the absorbent article and an outer surface facing away from the absorbent article. The absorbent article comprises a first leakage barrier side positioned along at least a part of the first longitudinal side edge and a second leakage barrier side positioned along at least a part of the second longitudinal side edge. The wrapper further comprises a cover portion covering the absorbent article and a first and a second flaps extending from the cover portion. The first and second flaps are folded over the liquid permeable first layer and are attached to each other securing each of the first and second leakage barrier sides in a folded position over at least a part of the liquid permeable first layer.

One advantage with the present invention is that the absorbent article can be positioned in an easily openable wrapper that allows for forming of the absorbent article into a cup shape upon opening the package. By securing each of the first and second leakage barrier sides in a folded position over a part of the liquid permeable first layer the absorbent article will keep its intended shape better and it is easier to achieve the desired cup shape.

By achieving the desired shape the absorbent article will follow the contours of a user's body better and the risk of side leakage is significantly reduced.

The first and second flaps of the absorbent article package may be extensions of the cover portion along each of the first and second longitudinal side edges and in a lateral direction.

The first and second flaps of the absorbent article package may be partly separated portions of the wrapper along each of the first and second longitudinal side edges being separated along separation lines extending in a lateral direction from the first and second longitudinal side edges towards the center line of the wrapper.

The flaps may thus be cut/slit parts of the wrapper and/or may be attached to the wrapper and/or may be extensions of the cover portion and/or the first and second longitudinal side edges.

A first part of the absorbent article may be at least partly folded over a second part of the absorbent article comprising the first and a second flaps.

A third part of the absorbent article may be at least partly folded over the second part of the absorbent article, wherein the absorbent article is at least triple folded within the package.

The first and second flaps of the absorbent article package may be positioned in connection to the first lateral side edge of the wrapper. Alternatively, the first and second flaps of the absorbent article package may be positioned at a predetermined distance from the first and second lateral side edges.

The wrapper of the absorbent article package may be folded over itself two times giving three layers of wrapper in a predetermined zone in connection to the first and second flaps. One advantage is that the slits in the wrapper from forming the first and second flaps may be covered by the folded parts.

The first and second flaps of the absorbent article package may be attached to each other with the inside of the wrapper against the outside of the wrapper. Alternatively, the first and second flaps of the absorbent article package may be attached to each other with the outside of the wrapper against the inside of the wrapper.

BRIEF DESCRIPTION OF DRAWINGS

The invention will now be described below in association to a number of drawings where.

EMBODIMENT(S) OF THE INVENTION

In FIGS. 1-10, the same reference numbers are used for like features.

In FIGS. 1-10 a longitudinal direction is labelled X, a lateral direction is labelled Y, and a thickness direction is labelled Z. This is shown in all figures with a three dimensional Cartesian coordinate system with axes X, Y, Z.

Figure 1:
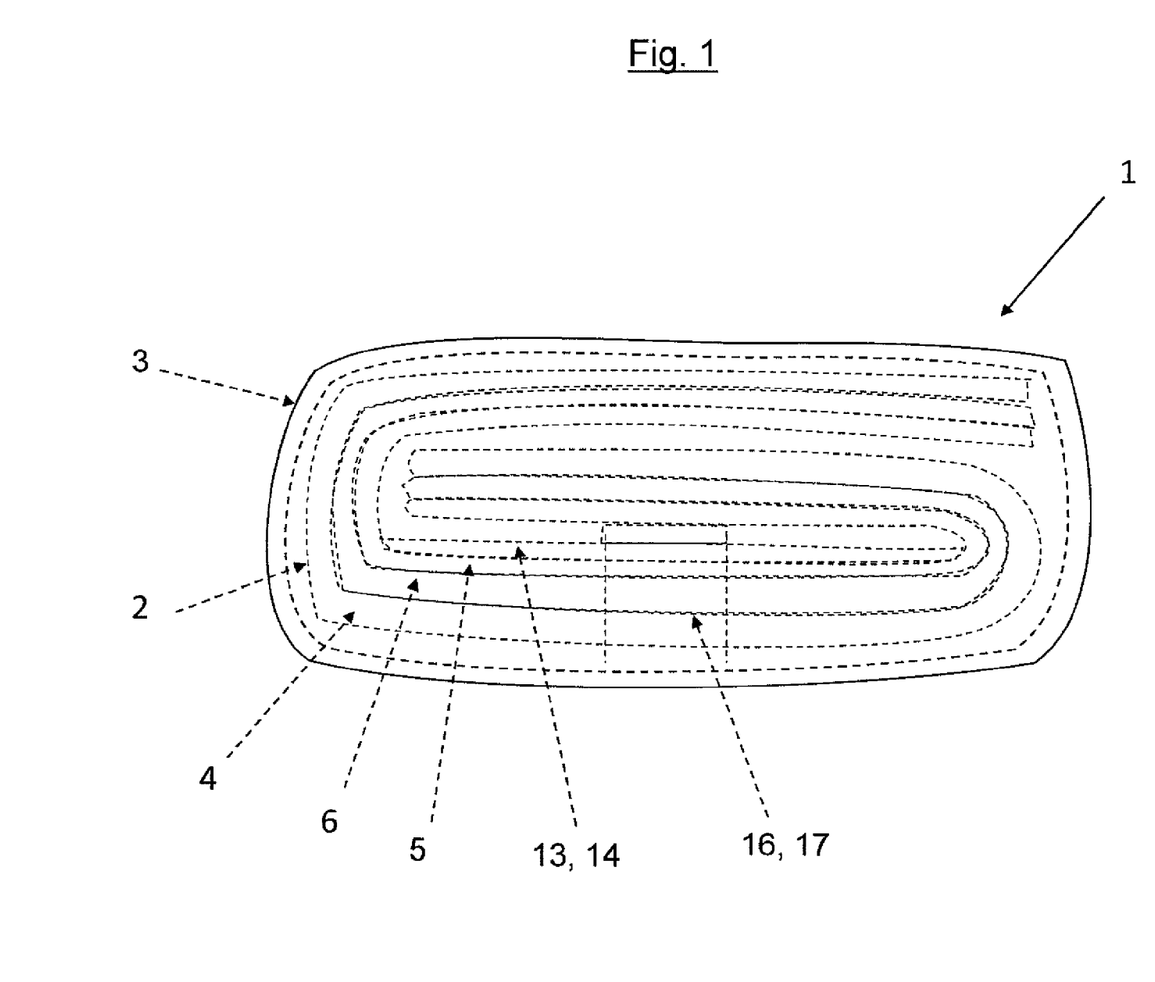
FIG. 1 schematically shows a side view of a folded absorbent article package according to an example of the invention.

FIG. 1 schematically shows an absorbent article package 1 according to a first example of the invention in a folded state. The absorbent article package 1 comprises an absorbent article 2 and a wrapper 3. The absorbent article 2 comprises a back sheet 4, a liquid permeable first layer 5 and an absorbent body 6 placed between the back sheet 4 and the liquid permeable first layer 5. In FIG. 1 the absorbent article 2 folded twice over itself and the wrapper 3 completely encloses the absorbent article 2 for protecting the absorbent article 2 from outside contaminants. It should be note that in the examples in FIGS. 2-10, the absorbent article may be packed non-folded, folded once or more, and the absorbent article can also be rolled. The wrapper 3 comprises a first flap 16 and a second flap 17. In FIG. 1 the flaps 16, 17 are folded over the liquid permeable first layer 5 and attached to each other securing each of first and second leakage barrier sides 13, 14.

Figure 2:
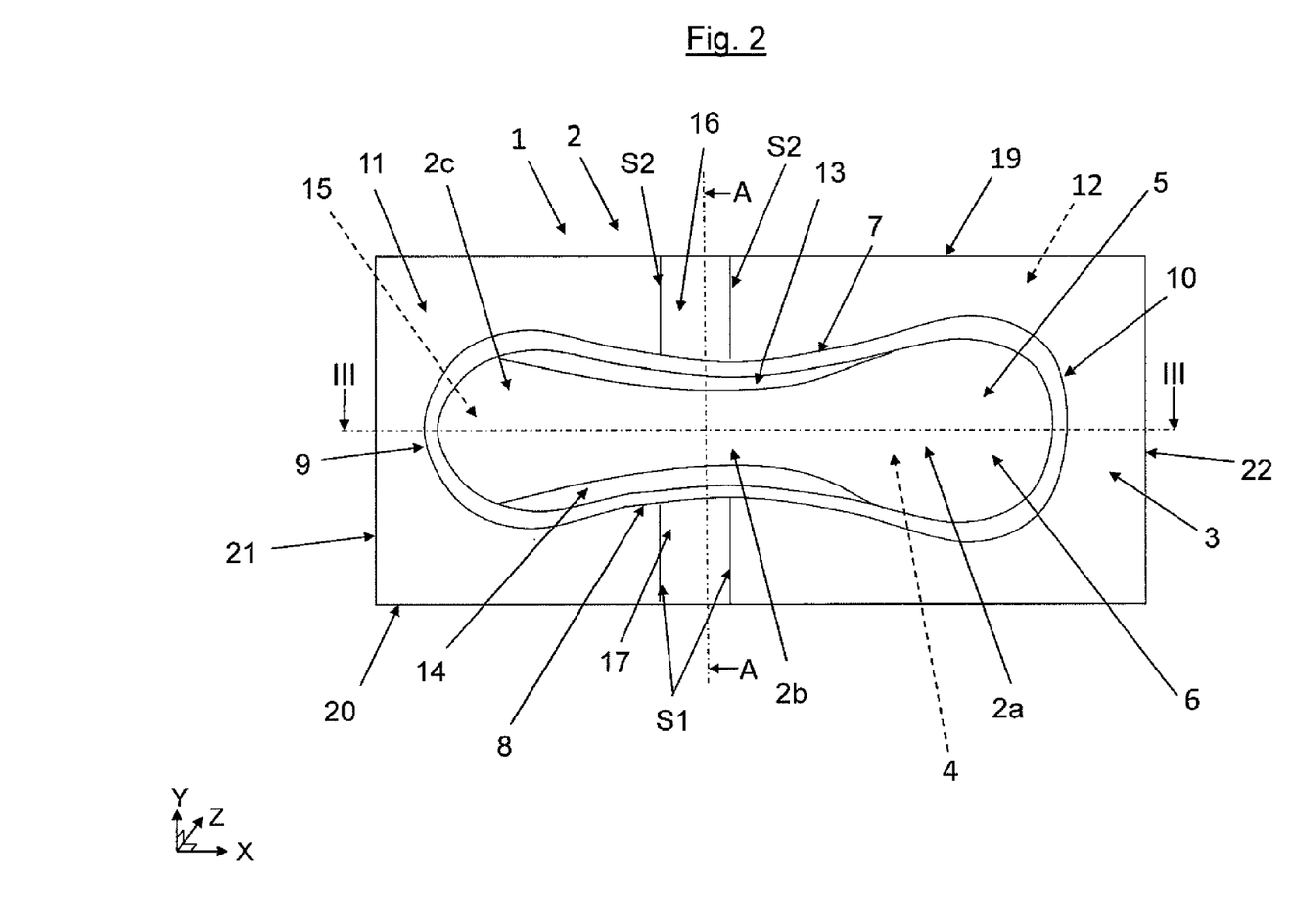
FIG. 2 schematically shows a top view of an opened absorbent and splayed absorbent article package according to a first example of the invention.

FIG. 2 schematically shows an absorbent article package 1 according to a first example of the invention in an open, splayed and unfolded state. In FIG. 2, the absorbent article package 1 comprises an absorbent article 2 and a wrapper 3. The absorbent article 2 comprises a back sheet 4, a liquid permeable first layer 5 and an absorbent body 6 placed between the back sheet 4 and the liquid permeable first layer 5. The back sheet 4 is preferably made of a liquid impervious polymeric film material. The backsheet may be breathable or non-breathable. The back sheet 4 of the absorbent article 2 may comprise fastening means (not shown) and is intended to be secured to an undergarment of the wearer. The fastening means may be a pressure sensitive hot melt adhesive. The liquid permeable first layer 5 is preferably made of nonwoven, a film or laminate thereof. The absorbent body 6 preferably comprises cellulose fluff pulp and may have superabsorbent material embedded in the cellulose fluff pulp. Other kinds of absorbent bodies are of course possible. For simplifying the description of the invention, the absorbent article is divided into a first part 2a, a second part 2b and a third part 2c. The first part 2a and/or the second part 2b or the second part 2b and/or the third part 2c may comprise the so called wetting zone, i.e. that part of the absorbent article that is intended to receive the main flow during urinal discharge of user. The absorbent article 2 is preferably cup shaped during use about the wetting zone in order to hinder side leakage. In the examples in FIGS. 2-10, the third part 2c is the front portion of the absorbent article 2 and the second part 2b is the crotch portion, but the invention is not limited to this since the third part could be a back portion of the absorbent article dependent on design. The front portion is intended to be positioned towards the front of the user, i.e. towards the lower abdomen. In the examples in FIGS. 2-10, the wetting zone is positioned in the second part 2b and the absorbent article becomes cup shaped accordingly during use.

The absorbent article 2 further comprises first and a second longitudinal side edges 7, 8 and first and second lateral side edges 9, 10 defining the extension of the absorbent article 2. In FIG. 2, the absorbent article 2 comprises a first leakage barrier side 13 positioned along at least a part of the first longitudinal side edge 7 and a second leakage barrier side 14 positioned along at least a part of the second longitudinal side edge 8. The first and second side leakage barrier sides 13, 14 are preferably positioned in connection to the wetting zone in order to enhance the side leakage protection. In FIG. 2, first and second side leakage barrier sides 13, 14 are positioned in the second part, but should the wetting zone be positioned in the third part 2c, or partly within the third part 2c and partly within the second part 2b, the first and second side leakage barrier sides 13, 14 would be positioned relative the wetting zone accordingly.

The wrapper 3 is preferably liquid-impervious, recyclable and/or biodegradable. Suitable materials include plastic films, nonwoven webs and laminates thereof. The wrapper 3 may be reinforced with additional materials located in various regions thereof. The wrapper 3 may comprise the release paper of the absorbent article (the release paper is the paper which covers any adhesive present on the backsheet prior to use). As such, the wrapper 3 functions as both release paper and packaging. As such, the wrapper 3 may be coated with a layer of e.g. silicone or similar agent which provides the wrapper with release properties. Alternatively, the wrapper 3 may be separate from the release paper.

The wrapper 3 may be releasably attached to the back sheet of the absorbent article 2 by means of the attachment means. The wrapper 3 has an inner surface 11 facing the absorbent article 2 and an outer surface 12 facing away from the absorbent article 2. The wrapper 3 has a first longitudinal side edge 19, a second longitudinal side edge 20, a first lateral side edge 21 and a second lateral side edge 22. The wrapper 3 further comprises a cover portion 15 covering the absorbent article 2 and is in direct contact with the absorbent article 2. In FIG. 2, the wrapper 3 shows that the first flap 16 and the second flap 17 are able to be folded over the liquid permeable first layer 5 and attached to each other securing each of the first and second leakage barrier sides 13, 14 in a folded position over a part of the liquid permeable first layer 5. The flaps 16, 17 may be cut/slit parts of the wrapper 3 and/or may be attached to the wrapper 3 and/or may be extensions of the cover portion and/or the first and second longitudinal side edges 7, 8. The first and second flaps 7, 8 are positioned along each of the first and second longitudinal side edges 7, 8 in the lateral direction of the absorbent article 2. In FIGS. 1-10 the first and second flaps 16, 17 are partly separated portions of the wrapper 3 along each of the first and second longitudinal side edges 19, 20 being separated along separation lines S1, S2 extending in a lateral direction from the first and second longitudinal side edges 19, 20 towards the center line of the wrapper 3. In FIG. 2, the first and a second flaps 16, 17 are positioned at a predetermined distance from the first and second lateral side edges 21, 22 of the wrapper, but may be positioned in connection to the first or second lateral side edge 21, 22 as shown in FIG. 4.

Figure 3:
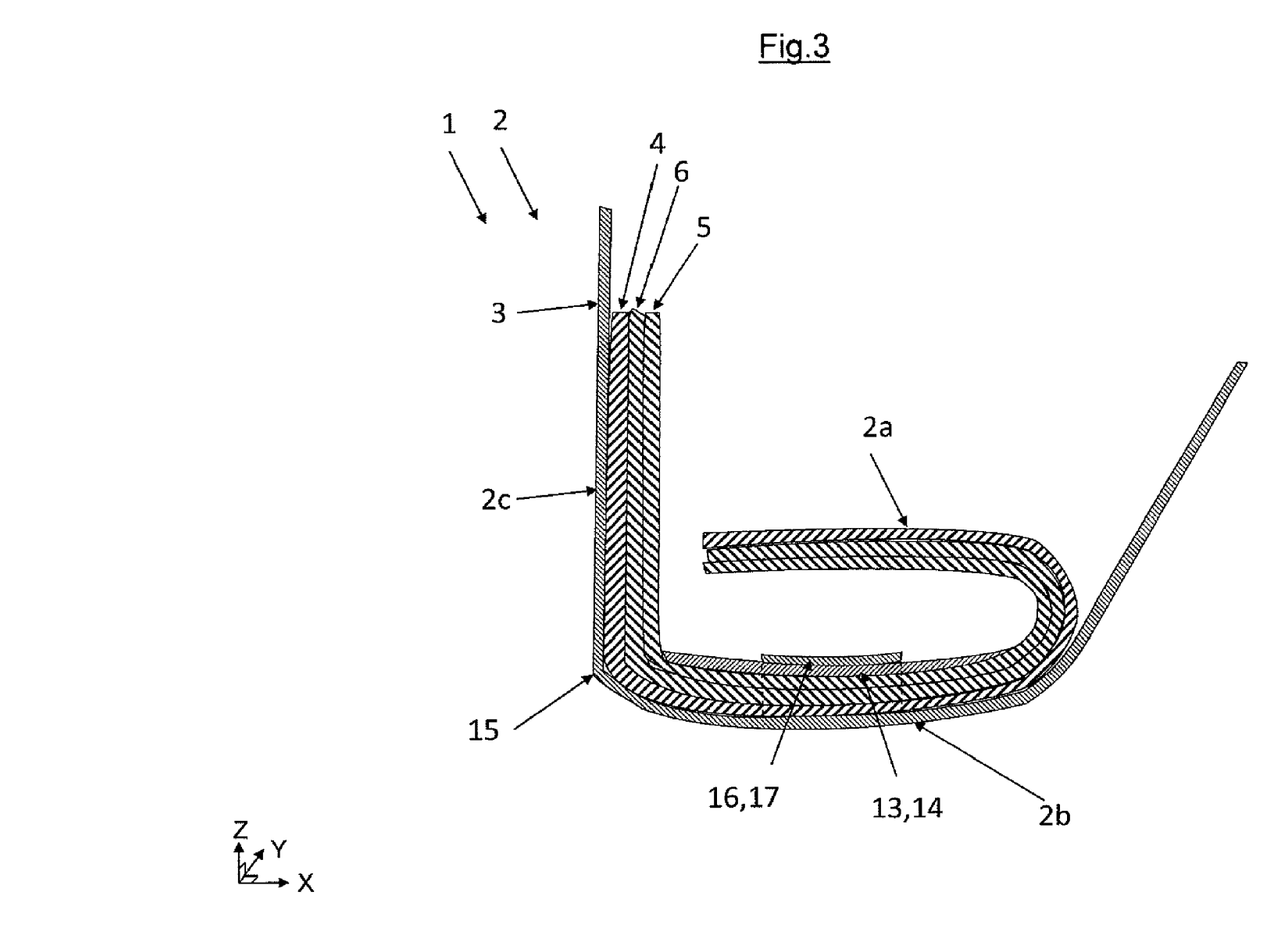
FIG. 3 schematically shows a side view of a partially folded absorbent article package according to a first example of the invention along the section III-III of FIG. 2.
Figure 4:
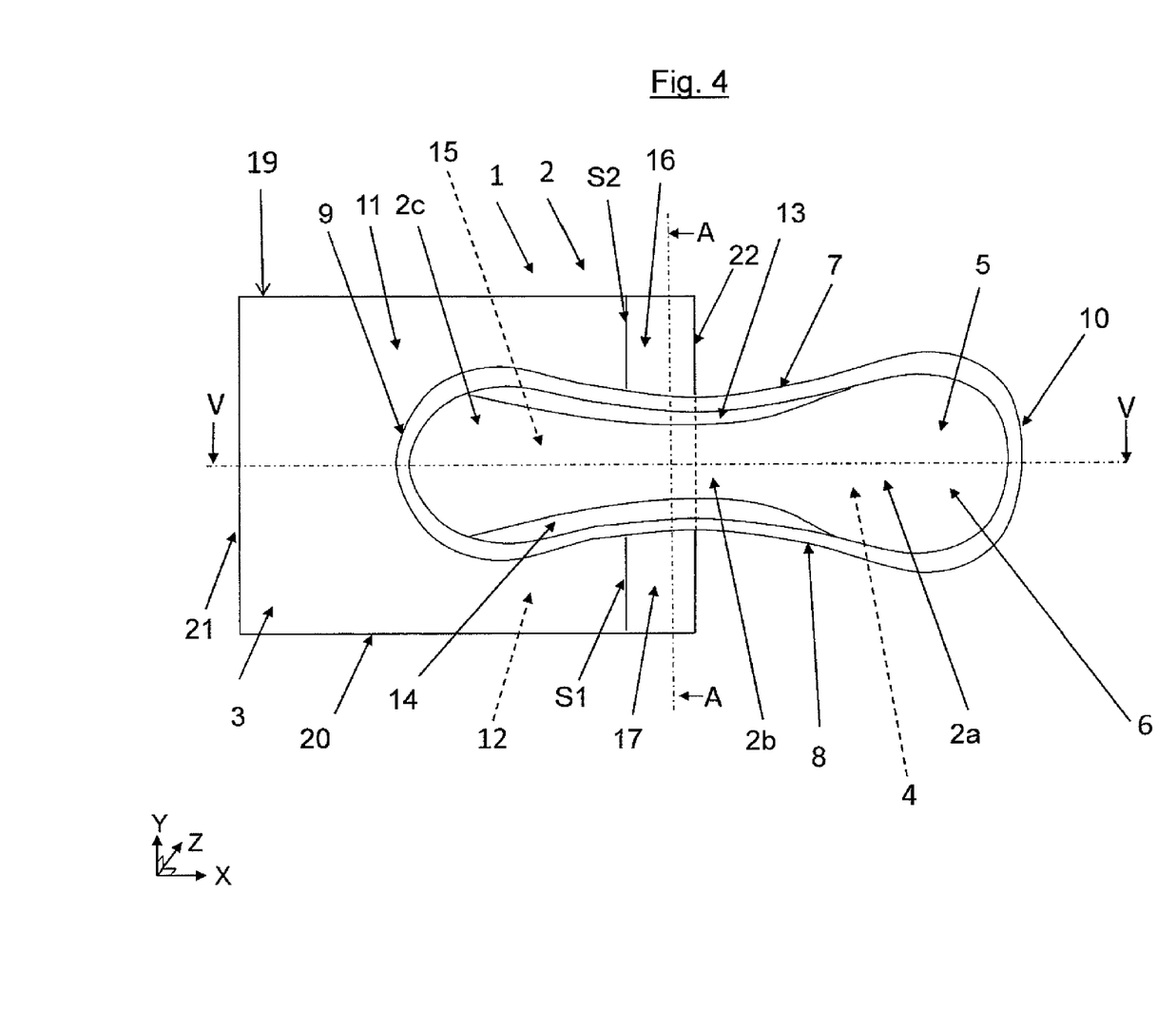
FIG. 4 schematically shows a top view of an opened absorbent and splayed absorbent article package according to a second example of the invention.

FIG. 3 shows the absorbent article package 1 in a partly folded state according to a first example of the invention along the section III-III of FIG. 2. The absorbent article package 1 is formed by first folding the first and second flaps 16, 17 over the liquid permeable first layer 5 thereby securing the first and second leakage barrier sides 13, 14 in a folded position over the liquid permeable first layer 5. Next the first part 2a of the absorbent article 2 is folded over the second part 2b of the absorbent article 2 followed by folding the third part 2c of the absorbent article 2 over the first and second parts 2a, 2b of the absorbent article 2. The folding order could be changed such that the third part 3c is folded over the second part 2c and then followed by the first part 2a. The folding could also be done by: folding a first portion of the first part 2a over a second portion of the first part 2a and a part of the second portion; and folding a first portion of the third part 2c over a second portion of the third part and a part of the second portion 2b; and then folding the folded first part 2a and folded third part 2c against each other over a folding line in the second part 2b. The wrapper 3 is then sealed into a package around the absorbent article 2 by means of welding, gluing, adhesive taping or any other suitable sealing means. As can be seen from FIG. 2 the first and second flaps 16, 17 are folded over the liquid permeable first layer 5 thereby securing the first and second leakage barrier sides 13, 14 in a folded position over the liquid permeable first layer 5.

FIG. 4 schematically shows the absorbent article package 1 according to a second example of the invention in an open, splayed and unfolded state. The difference between FIG. 2 is that in FIG. 4 the wrapper 3 extends only partly over the backsheet 4 and the second lateral edge 22 of the wrapper 3 is positioned in connection to the first and second flaps 16, 17. In FIG. 4 the first and second flaps 16, 17 are positioned in the second part 2b, but may be positioned in the first part 2a or the second part 2c, or in a transition area between the first and second parts 2a, 2b or in a transition area between the third and second parts 2c, 2b. The second lateral edge is thus position in the part(s) 2a, 2b, 2c accordingly and instead extends further in the longitudinal direction beyond the first lateral side edge 9 than in the previous example. Here the first and a second flaps 16, 17 are positioned in connection to the first lateral side edge 21 of the wrapper. The wrapper may be fastened to the absorbent article 2 via attachment means (not shown) on the backsheet 4. If the backsheet 4 comprises fastening means over an area not covered by the wrapper 3, a protective sheet (not shown) may be positioned on the fastening means in the first, second and/or third parts 2a, 2b, 2c of the absorbent article 2.

Figure 5:
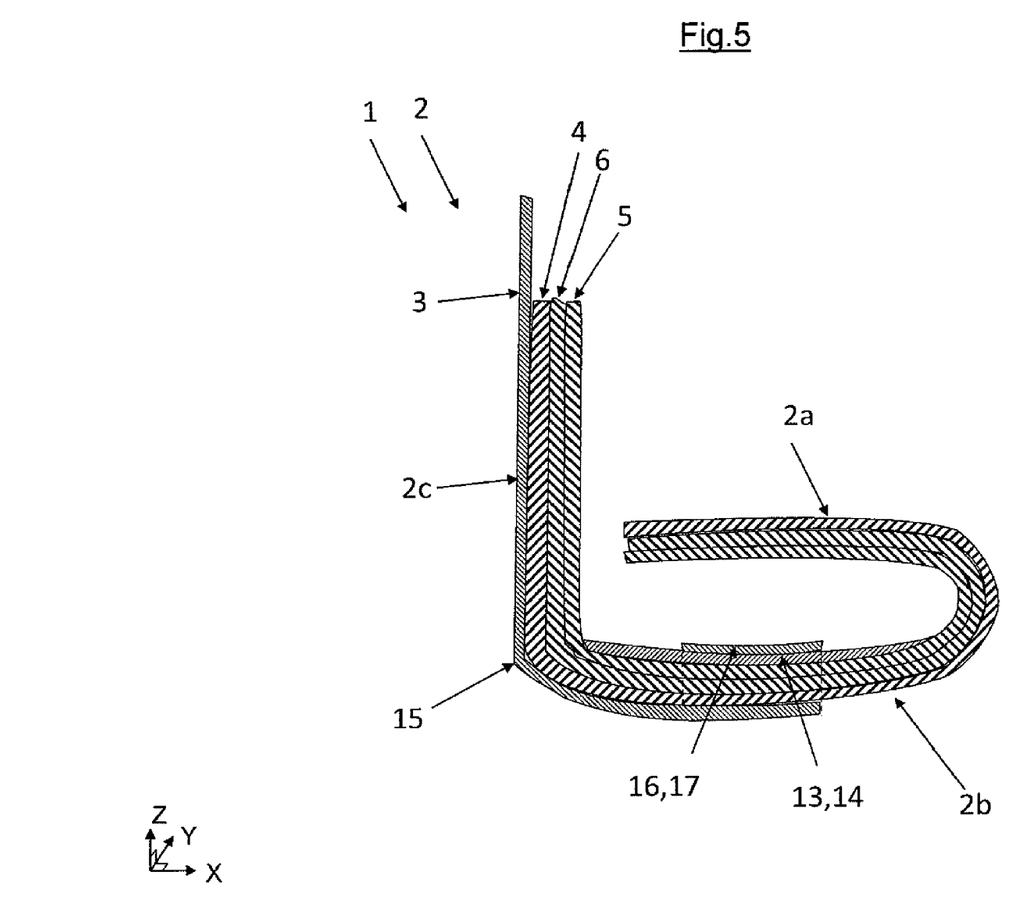
FIG. 5 schematically shows a side view of a partially folded absorbent article package according to a second example of the invention along the section V-V of FIG. 4.

FIG. 5 shows the absorbent article package 1 in a folded state according to a second example of the invention. The absorbent article package 1 shown is formed in a similar way as the absorbent article package shown in FIG. 3 by folding the first, second and third parts 2a, 2b, 2c dependent on the position of the first and second flaps 16, 17.

Figure 6:
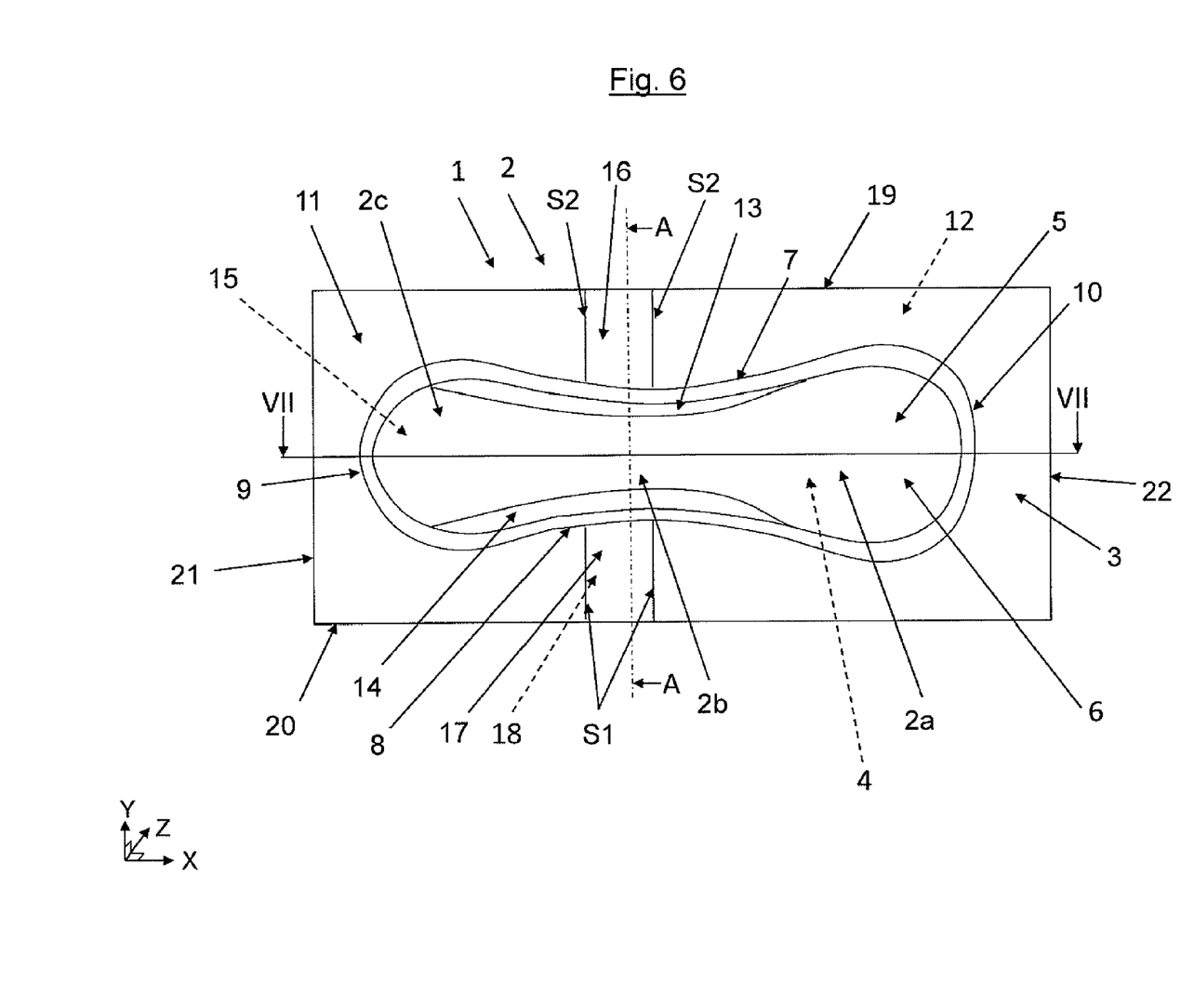
FIG. 6 schematically shows a top view of an opened absorbent and splayed absorbent article package according to a third example of the invention.

FIG. 6 schematically shows the absorbent article package 1 according to a third example of the invention in an open, splayed and unfolded state. The difference between FIG. 2 is that in FIG. 6 the wrapper 3 is a Z-folded, i.e. folded twice over itself giving a triple thickness, in a predetermined zone 18 being in connection to the first and second flaps 16, 17. The advantage with the Z-fold is that the slits S1 and S2 becomes covered by the folded parts during folding of the wrapper 3 into a package and thereby protects the absorbent article from outside contaminants. In the example in FIG. 2, the wrapper material is large enough to allow for folding over the slits, which means that the example in FIG. 6 also has the advantage of using less wrapper material and thus allowing the absorbent article package 1 to be narrower in the lateral direction while there is still sufficient material to form the package.

Figure 7:
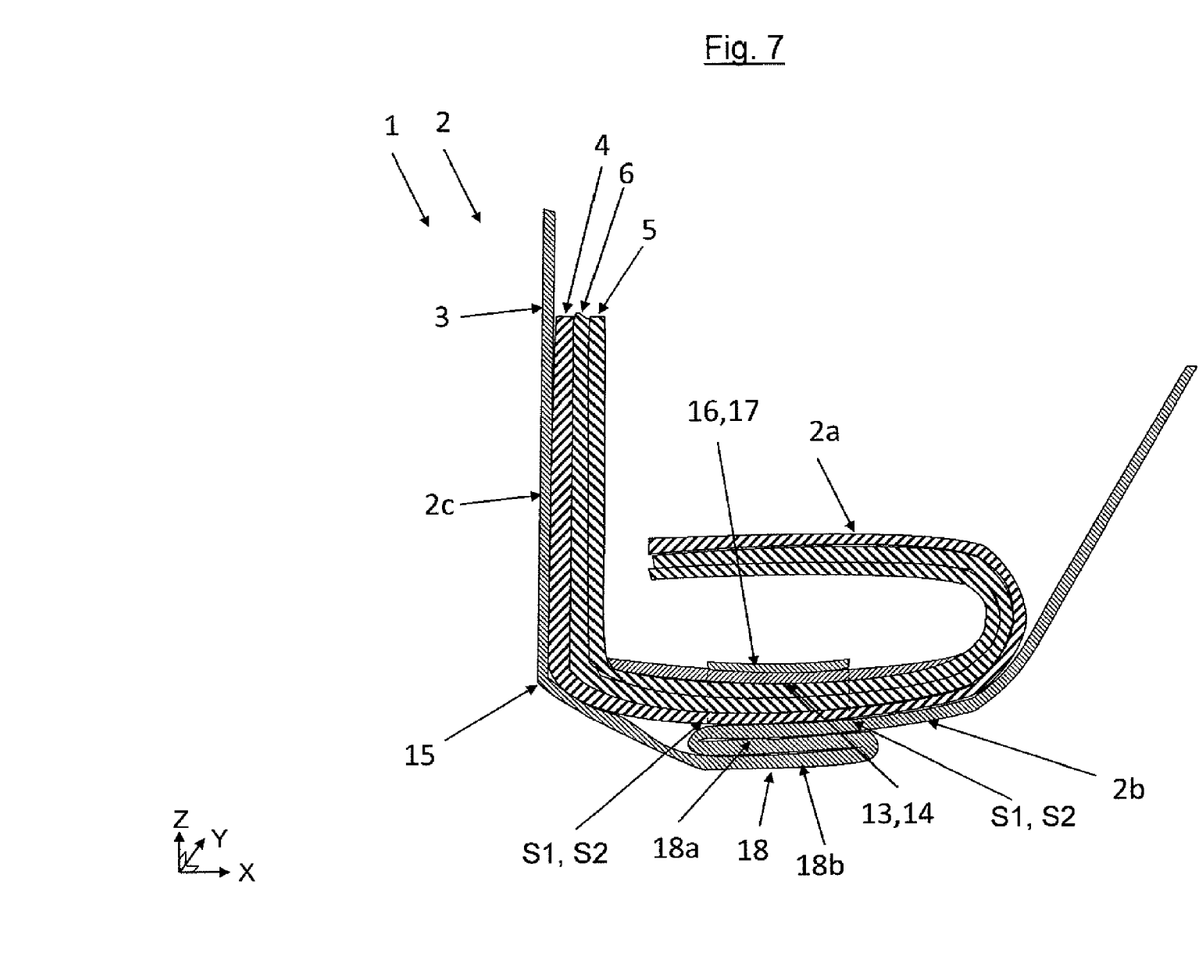
FIG. 7 schematically shows a side view of a partially folded absorbent article package according to a third example of the invention along the section VII-VII of FIG. 6.

FIG. 7 shows a side view along the section VII-VII in FIG. 6. As is shown the wrapper is folded over itself two times giving three layers of wrapper 3 in the predetermined zone 18 in connection to the first and a second flaps 16, 17. In FIG. 7 it is illustrated as a Z-fold 18 but other kinds of folds are possible. FIG. 7 shows that the folds are done along the slits S1 and S2 in order to allow the first and second flaps 16, 17 to be folded over the liquid permeable first layer 5 and attached to each other securing each of the first and second leakage barrier sides 13, 14. The first fold 18a is done along a first pair of opposing slits S1, S2 positioned on each side of the absorbent article and the second fold 18b is folded over the first fold 18a, along and over a second pair of opposing slits S1, S2. The second fold 18b preferably extends over the second set of slits S1, S2 on each side of the absorbent article 2 in order to cover the slits S1, S2 for protecting the absorbent article 2 from outside contaminants entering the package via the slits. The wrapper material used for the folds is taken from the same side of the chosen first pair of slits S1, S2. With reference to the example shown in FIGS. 4 and 5, the wrapper 3 could comprise a folding zone according to what has been shown in FIGS. 6 and 7.

Figure 8:
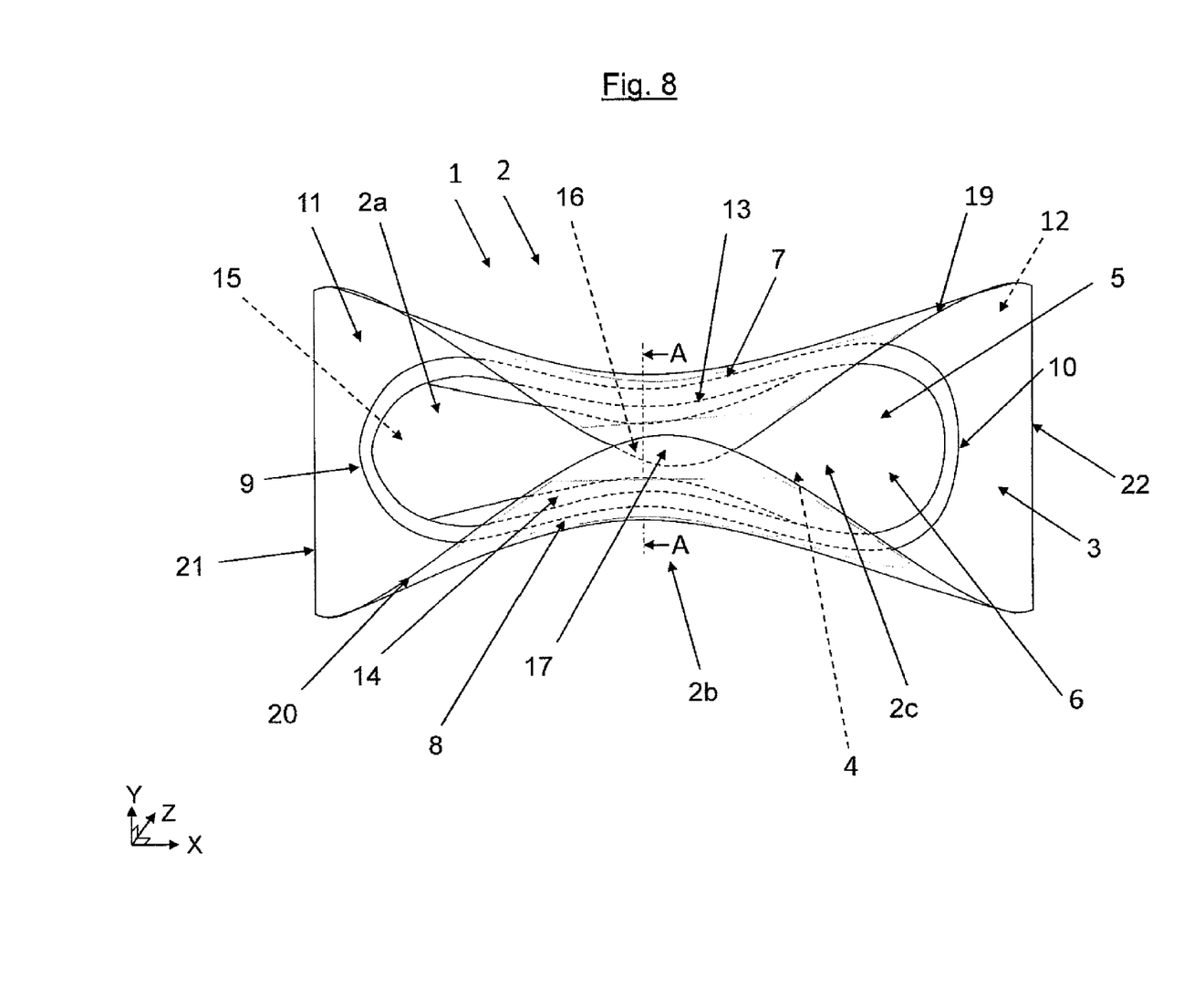
FIG. 8 schematically shows a top view of an opened absorbent and splayed absorbent article package according to a fourth example of the invention.

FIG. 8 schematically shows the absorbent article package 1 according to a fourth example of the invention in an open, splayed and unfolded state. In FIG. 8, the first and second flaps 16, 17 are extensions of the cover portion 15 along each of the first and second longitudinal side edges 7, 8 and in the lateral direction. FIG. 8 shows that the central parts of the longitudinal side edges 19, 20 of the wrapper 3 are folded over the liquid permeable first layer 5 and is used as the first and second flaps 16, 17 to secure each of the first and second leakage barrier sides 13, 14 in a folded position over a part of the liquid permeable first layer 5. One advantage with this example is that there is no slits in the wrapper that have to be covered to hinder outside contaminants to enter the package.

The wrapper 3 may in the central parts comprise laterally extending portions that can serve as, at least, parts of the first and second flaps 16, 17 to secure each of the first and second leakage barrier sides 13, 14 in a folded position over a part of the liquid permeable first layer 5.

The absorbent article package 1 according to the example in FIG. 8 can be made by folding the absorbent article and wrapper according to what has been described in connection to any one, or a combination of, FIGS. 1-8.

Figure 9:
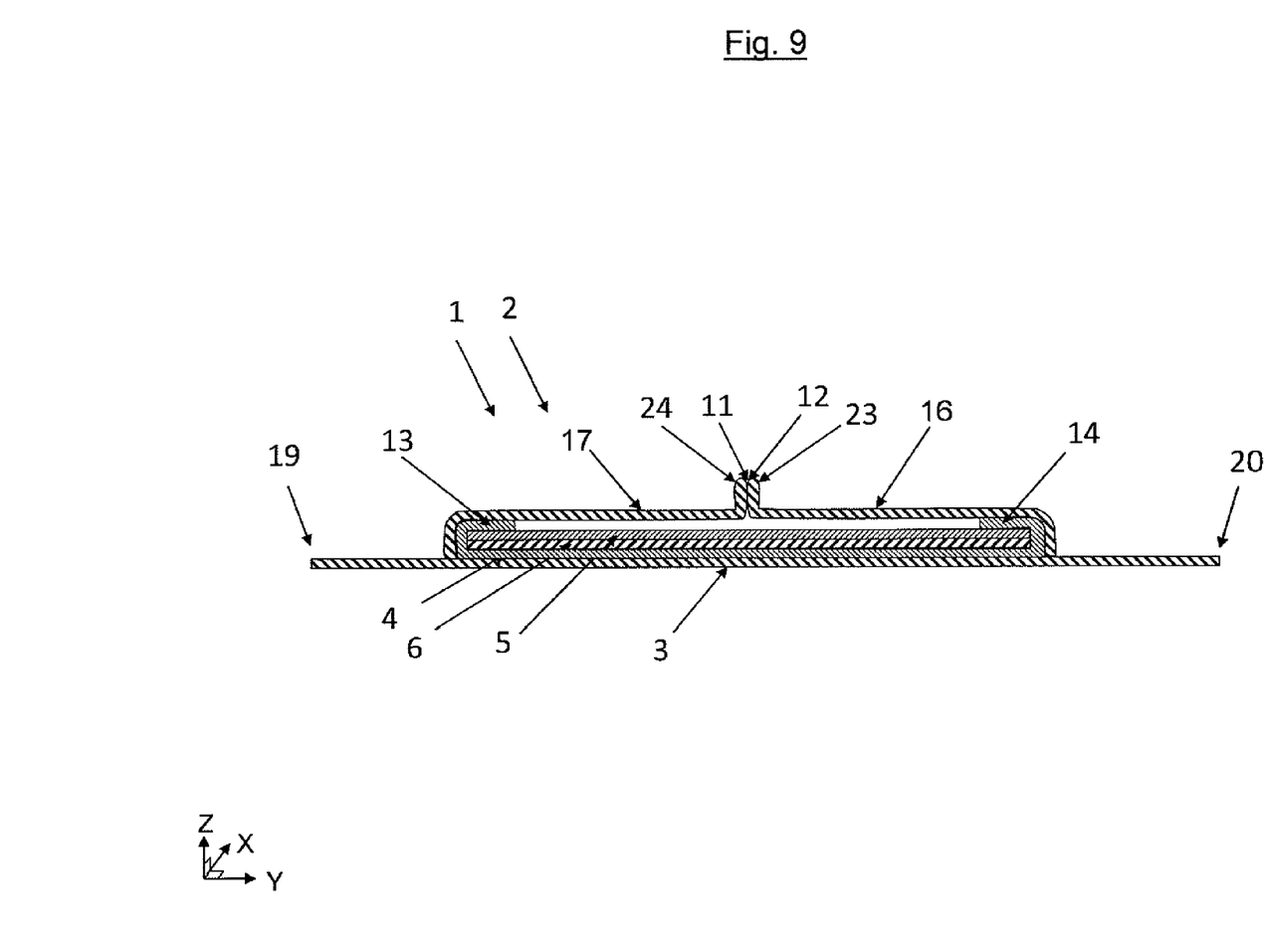
FIG. 9 schematically shows a view from a lateral side of an absorbent article package according to a fourth example of the invention.

FIG. 9 schematically shows the absorbent article along section A-A in FIGS. 2, 4, 6 and 8 according to a first aspect. Here it can be seen that the flaps 16, 17, according to FIGS. 1-7, or the central parts in connection to the longitudinal side edges 19, 20 of the wrapper 3, according to FIG. 8, are fastened to each other by folding a first edge portion 23 of the first flap 16 and a second edge portion 24 of the second flap 17 upwards and against each other with the inner surfaces 11 of the wrapper 3 attached to each other. For the embodiment in FIG. 8 parts of the longitudinal side edges 7, 8 of the wrapper 3 correspond to the first and second edge portions 23, 24 in FIGS. 2, 4 and 6, with regard to the fastening. The fastening may be done by any known fastening means; for example, welding, gluing, mechanically fastening means and adhesive (sticky) tape.

Figure 10:
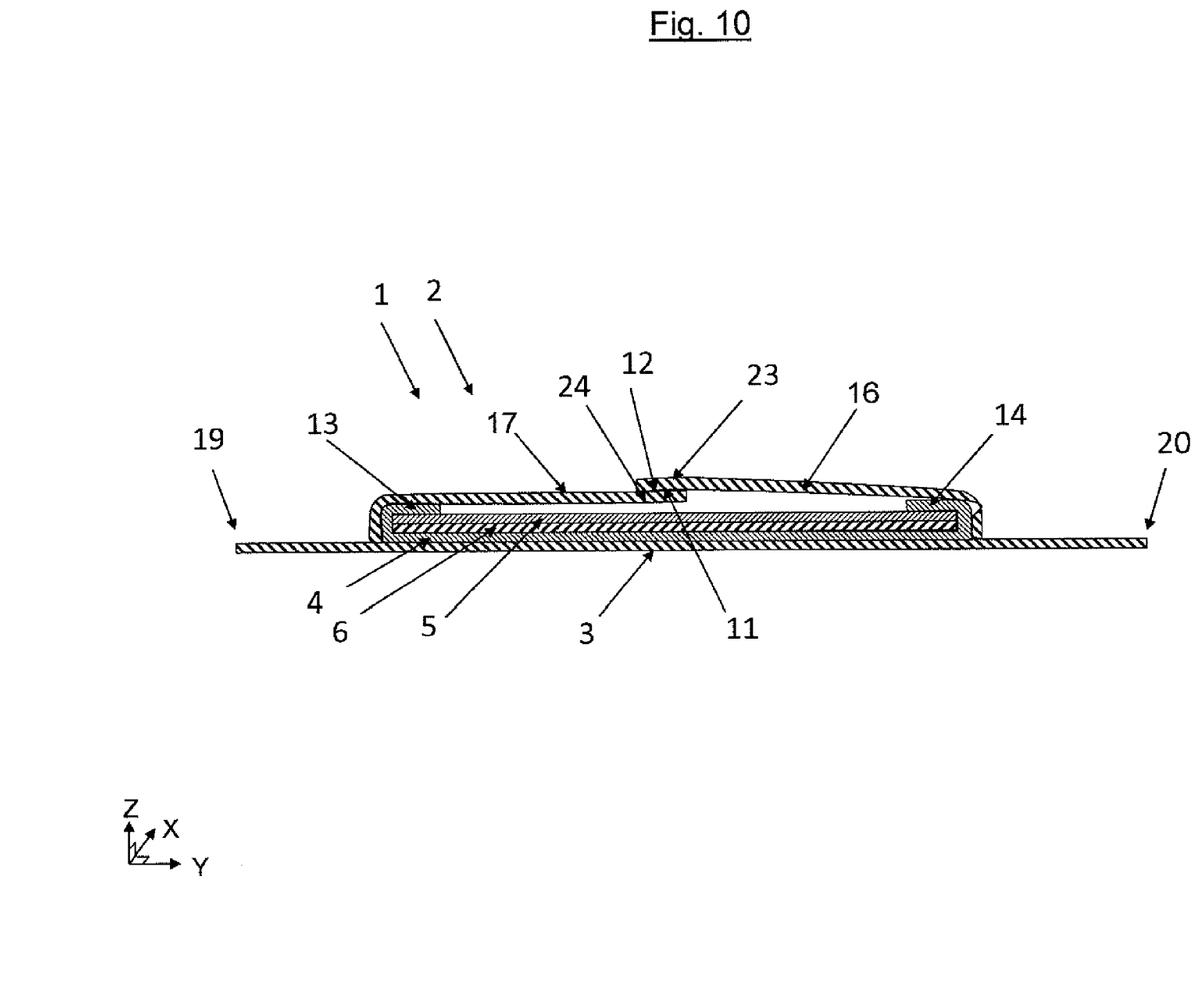
FIG. 10 schematically shows a view from a lateral side of an absorbent article package according to a fifth example of the invention.

FIG. 10 schematically shows the absorbent article along the section A-A in FIGS. 2, 4, 6 and 8. Here, it can be seen that the first and second flaps 16, 17, according to FIGS. 1-7, or the central parts in connection to the longitudinal side edges 19, 20 of the wrapper 3, according to FIG. 8, are fastened to each other by fastening the first flap 16 or side edge 19 of the wrapper 3 on top of the second flap 17 or side edge 20 of the wrapper 3. Here, the inner surface 11 of the wrapper 3 overlaps and is attached to the outside surface 12 of the wrapper 3. For the embodiment in FIG. 8 parts of the longitudinal side edges 7, 8 of the wrapper 3 correspond to the first and second edge portions 23, 24 in FIGS. 2, 4 and 6, with regard to the fastening. The fastening may be done by any known fastening means; for example, welding, gluing, mechanically fastening means and adhesive (sticky) tape.

Further variations are conceivable within the scope of the description. For instance the shape of the flaps 16, 17 or side edges 19, 20 may be varied in order to save material or for design reasons, etc.

The invention claimed is:

1. An absorbent article package comprising an absorbent article and a wrapper,
   the absorbent article comprising a backsheet, a liquid permeable first layer and an absorbent body therebetween, the absorbent article comprising opposing first and second longitudinal side edges and opposing first and second lateral side edges,
   the wrapper comprising an inner surface facing the absorbent article and an outer surface facing away from the absorbent article,
   the absorbent article comprising a first leakage barrier side positioned along at least a part of the first longitudinal side edge and a second leakage barrier side positioned along at least a part of the second longitudinal side edge,
   wherein the wrapper comprises a cover portion covering the absorbent article and wherein the wrapper comprises a first flap being folded along a first fold line, the first fold line being substantially parallel to the first longitudinal side edge and a second flap being folded along a second fold line, the second fold line being substantially parallel to the second longitudinal side edge, each flap being folded over the liquid permeable first layer and attached to each other securing each of the first and second leakage barrier sides in a folded position directly over a part of the liquid permeable first layer prior to use, wherein at least one of the first and second flaps are directly over at least one of the first and second leakage barrier sides, and wherein the first and second flaps are partly separated portions of the wrapper along each of the first and second longitudinal side edges, wherein the partly separate portions are separated along separation lines.

2. An absorbent article package according to claim 1, wherein the separation lines extend in a lateral direction from the first and second longitudinal side edges towards a center line of the wrapper.

3. An absorbent article package according to claim 1, wherein a first part of the absorbent article is folded over a second part of the absorbent article, the second part comprising the first and second flaps.

4. An absorbent article package according to claim 3, wherein a third part of the absorbent article is folded over the second part of the absorbent article, wherein the absorbent article is folded twice over to give three layers of the article within the package.

5. An absorbent article package according to claim 1, wherein the first and the second flaps are positioned connected to the first lateral side edge of the wrapper.

6. An absorbent article package according to claim 1, wherein the first and second flaps are positioned at a predetermined distance from the first and second lateral side edges.

7. An absorbent article package according to claim 6, wherein the wrapper is folded over itself two times giving three layers of wrapper in a predetermined zone in connection to the first and second flaps.

8. An absorbent article package according to claim 1, wherein the first and the second flaps are attached to each other with an inside of the wrapper against the inside of an opposing portion of the wrapper.

9. An absorbent article package according to claim 1, wherein the first and a second flaps are attached to each other with the outside of the wrapper against the inside of the wrapper.

10. An absorbent article package according to claim 1, wherein, after the flaps are folded over the liquid permeable first layer, a first part of the absorbent article is folded over a second part of the absorbent article, the second part comprising the folded first and second flaps.

11. An absorbent article package according to claim 10, wherein a third part of the absorbent article is folded over the second part of the absorbent article, wherein the absorbent article is folded twice over to give three layers of the article within the package.

12. An absorbent article package comprising an absorbent article and a wrapper,
   the absorbent article comprising a backsheet, a liquid permeable first layer and an absorbent body therebetween, the absorbent article comprising opposing first and second longitudinal side edges and opposing first and second lateral side edges,
   the wrapper comprising an inner surface facing the absorbent article and an outer surface facing away from the absorbent article,
   the absorbent article comprising a first leakage barrier side positioned along at least a part of the first longitudinal side edge and a second leakage barrier side positioned along at least a part of the second longitudinal side edge,
   wherein the wrapper comprises a cover portion covering the absorbent article and wherein the wrapper comprises a first flap being folded along a first fold line, the first fold line being substantially parallel to the first longitudinal side edge and a second flap being folded along a second fold line, the second fold line being substantially parallel to the second longitudinal side edge, each flap being folded over the liquid permeable first layer and attached to each other securing each of the first and second leakage barrier sides in a folded position over a part of the liquid permeable first layer, wherein the first and second flaps are partly separated portions of the wrapper along each of the first and second longitudinal side edges, wherein the partly separate portions are separated along separation lines,
   wherein, after the flaps are folded over the liquid permeable first layer, a first part of the absorbent article is folded over a second part of the absorbent article, the second part comprising the folded first and second flaps prior to use.

13. An absorbent article package according to claim 12, wherein a third part of the absorbent article is folded over the second part of the absorbent article, wherein the absorbent article is folded twice over to give three layers of the article within the package.

\* \* \* \* \*